United States Patent [19]
Hibst et al.

[11] Patent Number: 6,124,499
[45] Date of Patent: Sep. 26, 2000

[54] PREPARATION OF ORGANIC ACIDS SUCH AS ACRYLIC ACID BY CATALYTIC OXIDATION USING A GROUP V MIXED METAL OXIDE CATALYST CONTAINING CU, MO, W, V, NB AND TA

[75] Inventors: Hartmut Hibst, Schriesheim; Andreas Tenten, Maikammer; Laszlo Marosi, Ludwigshafen, all of Germany

[73] Assignee: BASF Aktiengesellschaft, Ludwigshafen, Germany

[21] Appl. No.: 09/199,487

[22] Filed: Nov. 25, 1998

Related U.S. Application Data

[62] Division of application No. 08/685,490, Jul. 24, 1996, Pat. No. 5,885,922.

[30] Foreign Application Priority Data

Aug. 4, 1995 [DE] Germany .......................... 195 28 646

[51] Int. Cl.[7] .................................................. C07C 51/16
[52] U.S. Cl. .......................... 562/535; 562/547; 562/538; 502/305; 502/313; 502/321; 502/306; 502/307
[58] Field of Search ...................................... 562/547, 535

[56] References Cited

U.S. PATENT DOCUMENTS

| | | |
|---|---|---|
| 4,035,262 | 7/1977 | Childress et al. . |
| 5,686,373 | 11/1997 | Tenten et al. . |

FOREIGN PATENT DOCUMENTS

| | | |
|---|---|---|
| 0 000 835 | 2/1979 | European Pat. Off. . |
| 0 293 859 | 12/1988 | European Pat. Off. . |
| 0 575 897 | 12/1993 | European Pat. Off. . |
| 0 668 102 | 8/1995 | European Pat. Off. . |
| 0 668 103 | 8/1995 | European Pat. Off. . |
| 2 201 528 | 11/1972 | Germany . |
| 28 30 765 | 1/1980 | Germany . |
| 29 09 671 | 10/1980 | Germany . |
| 33 38 380 | 4/1984 | Germany . |
| 42 20 859 | 1/1994 | Germany . |
| 44 07 020 | 9/1994 | Germany . |
| 43 35 973 | 4/1995 | Germany . |
| 44 05 058 | 8/1995 | Germany . |
| 44 05 059 | 8/1995 | Germany . |
| 44 05 060 | 8/1995 | Germany . |
| 44 05 514 | 8/1995 | Germany . |
| 44 40 891 | 5/1996 | Germany . |

OTHER PUBLICATIONS

JCPDS–ICDD index cards, Set 42, Powder Diffraction File, Inorganic and Organic, International Centre for Diffraction, 1989.
Inorg. Chem. 1986, 25, 3782–3785, Hydrothermal Synthesis of Copper Molybdates; Ahmad Moini, et al, Apr. 11, 1986.
Russian Journal of Inorganic Chemistry 36 (7) 1991, "The crystal structure of $CuMoO_4$–III", R. Tali, et al.

*Primary Examiner*—Paul J. Killos
*Assistant Examiner*—Robert W. Deemie
*Attorney, Agent, or Firm*—Oblon, Spivak, McClelland, Maier & Neustadt, P.C.

[57] ABSTRACT

Multimetal oxide materials containing molybdenum, vanadium, copper and one or more of the elements tungsten, niobium, tantalum, chromium and cerium and having a multiphase structure, and their use for the preparation of acrylic acid from acrolein by gas-phase catalytic oxidation, and oxometallates of the HT Cu molybdate structure type which contain Cu, Mo and at least one of the elements W, V, Nb and Ta.

57 Claims, No Drawings

PREPARATION OF ORGANIC ACIDS SUCH AS ACRYLIC ACID BY CATALYTIC OXIDATION USING A GROUP V MIXED METAL OXIDE CATALYST CONTAINING CU, MO, W, V, NB AND TA

This application is a division of Ser. No. 08/685,490, filed Jul. 24, 1996 now U.S. Pat. No. 5,885,922.

BACKGROUND OF THE INVENTION

1. Field of the Invention

The present invention relates to multimetal oxide materials of the general formula I $$[A]_p[B]_q, \quad (I)$$

where

A is $\underset{12}{Mo} \; V_a \; X^1_b \; X^2_c \; X^3_d \; X^4_e \; X^5_f \; X^6_g \; O_x$ (active phase), B is $X^7_{12} \; Cu_h \; H_i \; o_y$ (promoter phase), $X^1$ is W, Nb, Ta, Cr and/or Ce, preferably W, Nb and/or Cr,
$X^2$ is Cu, Ni, Co, Fe, Mn and/or Zn, preferably Cu, Ni, Co and/or Fe,
$X^3$ is Sb and/or Bi, preferably Sb,
$X^4$ is Li, Na, K, Rb, Cs and/or H, preferably Na and/or K,
$X^5$ is Mg, Ca, Sr and/or Ba, preferably Ca, Sr and/or Ba,
$X^6$ is Si, Al, Ti and/or Zr, preferably Si, Al and/or Ti,
$X^7$ is Mo, W, V, Nb and/or Ta, preferably Mo and/or W,
a is from 1 to 8, preferably from 2 to 6,
b is from 0.2 to 5, preferably from 0.5 to 2.5,
c is from 0 to 23, preferably from 0 to 4,
d is from 0 to 50, preferably from 0 to 3,
e is from 0 to 2, preferably from 0 to 0.3,
f is from 0 to 5, preferably from 0 to 2,
g is from 0 to 50, preferably from 0 to 20,
h is from 4 to 30, preferably from 6 to 24, particularly preferably from 9 to 17,
i is from 0 to 20, preferably from 0 to 10,
x and y are each numbers which are determined by the valency and frequency of the elements other than oxygen in I and
p and q are non-zero numbers whose ratio p/q is from 160:1 to 1:1, preferably from 20:1 to 1:1, particularly preferably from 15:1 to 4:1,
which contain the component $[A]_p$ in the form of three-dimensional regions A which are delimited with respect to their local environment owing to their chemical composition differing from their local environment and are of the chemical composition A is $Mo_{12} \; V_a \; X^1_b \; X^2_c \; X^3_d \; X^4_e \; X^5_f \; X^6_g \; O_x$ and the component $[B]_q$ in the form of three-dimensional regions B which are delimited from their local environment owing to their chemical composition differing from their local environment and are of the chemical composition B is $X^7_{12} \; Cu_h \; H_i \; o_y$ where the regions A and B are distributed relative to one another as in a mixture of finely divided A and finely divided B, with the proviso that the regions B contain crystallites of oxometallates of the general formula II $$Cu \; Mo_A \; W_B \; V_C \; Nb_D \; Ta_E \; O_Y, \quad (II)$$

where
1/(A+B+C+D+E) is from 0.7 to 1.3, preferably from 0.85 to 1.15, particularly preferably from 0.95 to 1.05, very particularly preferably 1,
(B+C+D+E)/A is from 0.01 to 1, preferably from 0.05 to 0.3, particularly preferably from 0.075 to 0.15 and very particularly preferably 0.11 and
Y is a number which is determined by the valency and frequency of the elements other than oxygen in II,
of a novel structure type which is defined below by means of its X-ray diffraction pattern (fingerprint). The characteristic and most intense diffraction lines of the novel structure type are shown in the form of interplanar spacings d[Å] independent of the wavelength of the X-rays used:

| d [Å] | Intensity [%] |
|---|---|
| 3.40 + 0.3 | 100 |
| 3.54 + 0.3 | 72 |
| 2.27 + 0.2 | 39 |
| 6.79 + 0.3 | 32 |
| 2.56 + 0.2 | 25 |
| 1.57 + 0.2 | 22 |
| 1.87 + 0.2 | 19 |
| 2.96 + 0.3 | 18 |
| 3.56 + 0.3 | 18 |
| 1.64 + 0.2 | 17 |
| 2.66 + 0.2 | 16 |
| 1.59 + 0.2 | 16 |
| 1.55 + 0.2 | 16 |
| 2.67 + 0.2 | 14 |
| 2.00 + 0.2 | 14 |
| 3.04 + 0.3 | 13 |
| 1.57 + 0.2 | 11 |
| 2.36 + 0.2 | 11 |
| 1.44 + 0.2 | 11 |
| 1.70 + 0.2 | 10 |
| 1.51 + 0.2 | 10 |
| 2.35 + 0.2 | 10 |

The stated intensities are relative reference values and are based on the diffraction line having the strongest intensity. Intensity is understood here as meaning the maximum amplitude of the X-ray diffraction band. The associated diffraction angles Θ are obtained from the Bragg relationship:

$$\sin \Theta = \lambda/2d,$$

where λ is the wavelength of the X-rays used for X-ray diffraction. The above data are based on the powder pattern of an oxometallate $Cu_1 \; Mo_{0.9} \; W_{0.1} \; O_4$. The corresponding X-ray pattern was produced on a Siemens D-5000 diffractometer using Cu Kα radiation (40 kV, 30 mA, λ=1.5406 Å). The diffractometer was equipped with an automatic divergence, antidiffusion and counter collimator and a Peltier detector. Regarding the stated line intensities, it should be noted that, in contrast to the position of the lines, the relative line intensities are markedly influenced, in a manner known per se to a person skilled in the art, by the individual crystal orientations established in various preparations for powder analysis, on the basis of the anisotropy of the crystal form, and are therefore less significant for identification of the novel structure type. The quantitative intensities stated above are therefore to be understood as typical values which may vary by up to ±50% (based on the stated values) in the case of the lines of strongest intensity (30–100%, based on the line of strongest intensity).

The novel structure type is to be defined below as HT (High Temperature) copper molybdate type, and crystallites of oxometallates II of the novel structure type defined above are to be referred to as crystallites B*.

The present invention also relates to the oxometallates II themselves and processes for the preparation of oxometallates II and of multimetal oxide materials I.

The present invention furthermore relates to the use of oxometallates II or multimetal oxide materials I for catalytic gas-phase oxidations of low molecular weight organic compounds.

2. Description of the Background

DE-A 4 335 973 and U.S. Pat. No. 4,035,262 relate to multimetal oxide materials whose empirical elemental composition corresponds to that of the novel multimetal oxide materials. These multimetal oxide materials are prepared by processing suitable sources of the components of the desired multimetal oxide materials in the required amounts to give an intimate dry mixture and then calcining the latter at elevated temperatures for several hours. The resulting multimetal oxide materials are recommended as catalysts for the preparation of acrylic acid from acrolein by gas-phase catalytic oxidation. However, the disadvantage of the prior art multimetal oxide materials is that during their use, the selectivity of the acrylic acid formation at a given acrolein conversion is not completely satisfactory. Furthermore, these multimetal oxide materials exhibit pronounced forming behavior, ie., when freshly prepared multimetal oxide materials are used, the selectivity (at a given acrolein conversion) of the acrylic acid formation reaches its final value only after a relatively long operating time, and said final value then remains essentially stationary. Furthermore, the reproducibility of their preparation with respect to the stationary final value of the selectivity of the acrylic acid formation is unsatisfactory.

EP-A 835, DE-C 3 338 380, DE-A 4 220 859 and DE-A 4 307 381 also relate to multimetal oxide materials which are suitable as catalysts for the preparation of α,β-monoethylenically unsaturated carboxylic acids by gas-phase catalytic oxidation and which advantageously have a co-phase/key phase structure. Although the general formulae of this prior art also formally include, within a broad diversity of possible multimetal oxide materials, those whose key phase can simultaneously contain the element copper in addition to elements such as molybdenum or tungsten, the totality of all embodiments comprises not a single such embodiment; rather, said embodiments are limited to those whose key phase contains the element bismuth instead of the element copper. The prior art expressly recommends this embodiment as the particularly preferred one. The disadvantage of this preferred embodiment of the prior art, however, is that it too is not completely satisfactory as a catalyst for the catalytic gas-phase oxidation of acrolein to acrylic acid, with regard to the selectivity of the acrylic acid formation at a given acrolein conversion.

The prior applications DE-A 44 05 058, DE-A 44 05 059 and DE-A 44 05 060 relate to multimetal oxide materials which likewise have a co-phase/key phase structure. They are particularly suitable for the preparation of methacrylic acid by gas-phase catalytic oxidation but are unsatisfactory for the catalytic gas-phase oxidation of acrolein to acrylic acid, with regard to the selectivity of the acrylic acid formation at a given acrolein conversion.

The prior application DE-A 44 05 514 and the prior application DE-A 44 40 891 relate to multimetal oxide materials which likewise have a co-phase/key phase structure $[A']_p$, $[B']_q$, the empirical elemental compositions of the co-phase and of the key phase there each being in agreement with the empirical elemental compositions of the active phase and of the promoter phase of the multimetal oxide materials I of the present invention. The two abovementioned prior applications furthermore state that the key phases B' there may contain crystallites which have the structure type (the X-ray diffraction pattern) of at least one of the copper molybdates listed in Table 1 below (the expression in brackets indicates the source of the associated X-ray diffraction fingerprint):

TABLE 1

| | |
|---|---|
| $Cu_3(MoO_4)_2(OH)_2$ | (lindgrenite, index card 36-405 of the JCPDS-ICDD index (1991)), |
| $Cu_4MoO_6O_{20}$ | (A. Moini et al., Inorg. Chem. 25 (21) (1986) pages 3782 to 3785), |
| $Cu_4Mo_5O_{17}$ | (index card 39-181 of the JCPDS-ICDD index (1991)), |
| $Cu_6Mo_5O_{18}$ | (index card 40-865 of the JCPDS-ICDD index (1991)), |
| $Cu_6Mo_4O_{15}$ | (index card 35-17 of the JCPDS-ICDD index (1991)), |
| $CuMoO_4$ | (index card 22-242 of the JCPDS-ICDD index (1991)), |
| $CuMoO_4$ | (Russian Journal of Inorganic Chemistry 36 (7), (1991), 927-928, Table 1, Cu Mo O₄-III with distorted wolframite structure ($CuWO_4$, index card 21-307 of the JCPDS-ICDD index (1994)), |
| $Cu_{4-x}Mo_3O_{12}$ | where x = 0 to 0.25 (index cards 24-56 and 26-547 of the JCPDS-ICDD index (1991)), |
| $Cu_3Mo_2O_9$ | (index cards 24-55 and 34-637 of the JCPDS-ICDD index (1991)), |
| $Cu_2MoO_5$ | (index card 22-607 of the JCPDS-ICDD index (1991)). |

Multimetal oxide catalysts $[A']_p$, $[B']_q$ which are recommended by DE-A 44 05 514 and DE-A 44 40 891 as being particularly advantageous for the catalytic gas-phase oxidation of acrolein to acrylic acid are those multimetal oxide materials whose key phase contain crystallites of oxometallates of the general formula III $$CuMo_{A'}W_{B'}V_{C'}Nb_{D'}Ta_{E'}O_{Y'}\cdot(H_2O)_{F'}, \qquad (III)$$

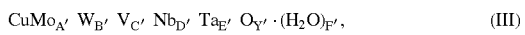

where $1/(A'+B'+C'+D'+E')$ is from 0.7 to 1.3,

F' is from 0 to 1,

B'+C'+D'+E' is from 0 to 1 and

Y' is a number which is determined by the valency and frequency of the elements other than oxygen in III, of the structure type which is defined by the compound $CuMoO_4$—III in Table 1 in Russian Journal of Inorganic Chemistry 36(7) (1991), 921, and was designated as wolframite in the DE-As.

At the time of filing of DE-A 44 05 514 and of DE-A 44 40 891, the fact that the HT copper molybdate structure type existed at all was unknown, to say nothing of the fact that special oxometallates III, ie. the oxometallates II, occur in this structure type. The fact that the novel multimetal oxide materials I whose promoter phase B contains crystallites of oxometallates II in the HT copper molybdate structure type can particularly advantageously be used as catalysts for the gas-phase catalytic oxidation of acrolein to acrylic acid was also unknown.

SUMMARY OF THE INVENTION

Accordingly, the abovementioned forms the subject of the present invention.

Very particularly preferred materials I are those whose regions A have a composition of the following general formula IV $$Mo_{12} V_{a'} X^1_{b'} X^2_{c'} X^3_{d'} X^4_{e'} X^5_{f'} X^6_{g'} O_{x'}, \quad (IV)$$

where $X^1$ is W and/or Nb,
$X^2$ is Cu and/or Ni,
$X^5$ is Ca and/or Sr,
$X^6$ is Si and/or Al,
a' is from 2 to 6,
b' is from 1 to 2,
c' is from 1 to 3,
f' is from 0 to 0.75,
g' is from 0 to 10 and
x' is a number which is determined by the valency and frequency of the elements other than oxygen in IV.

It is also advantageous if the component $[B]_q$ of the novel multimetal oxide materials I is present in the latter in the form of three-dimensional regions of the chemical composition B whose largest diameter $d_B$ (longest distance between two points on the surface (interface) of the region, passing through the center of gravity of the region) are from >0 to 300 μm, preferably from 0.1 to 200 μm, particularly preferably from 0.5 to 50 μm, very particularly preferably from 1 to 30 μm. However, the largest diameters may of course also be from 50 to 150 μm or from 75 to 125 μm (experimental determination of the largest diameters to be carried out, for example, by the method of laterally resolved energy dispersive X-ray spectroscopy (EDXS), for example by means of an electron beam microprobe JEOL JCXA/733).

The component $[A]_p$ may be present in amorphous and/or crystalline form in the novel multimetal oxide materials I. The component $[B]_q$ may consist exclusively of oxometallate II crystallites of the novel structure type, as well as comprising crystallites having a composition $$X^7_{12} Cu_h H_i O_y$$

of one (or more) other structure types, in particular of those stated in Table 1. The component $[B]_q$ can of course also contain amorphous compositions $$X^7_{12} Cu_h H_i O_y$$

The amount of the crystallites B* may therefore be from >0 to 100 or from 1 to 95 or from 5 to 90 or from 10 to 85 or from 15 to 75 or from 25 to 65 or from 35 to 55 or from 40 to 50, % by weight, based on the total amount of the component $[B]_q$. An amount of from 95 to 100% by weight is of course also suitable.

Crystallites B* which are particularly suitable according to the invention are those of the stoichiometry II where C+D+E=0, ie. oxometallates II of the novel structure type which are advantageous according to the invention are those of the general formula V $$Cu\ Mo_A\ W_B\ O_Y, \quad (V)$$

where
1/(A+B) is from 0.7 to 1.3, preferably from 0.85 to 1.15, particularly preferably from 0.09 to 1.05, very particularly preferably 1,
B/A is from 0.01 to 1, preferably from 0.05 to 0.2, particularly preferably from 0.075 to 0.15, very particularly preferably 0.11, and
Y is a number which is determined by the valency and frequency of the elements other than oxygen in V, frequently from 3.5 to 4,
ie. a very particularly advantageous novel oxometallate II of the novel structure type has the composition $$Cu_1\ Mo_{0.9}\ W_{0.1}\ O_{3.5-4}.$$

The novel materials I are obtainable in a simple manner, for example by pre-forming, separately in finely divided form, a multimetal oxide material $$X^7_{12} Cu_h H_i O_y, \quad (B)$$

which contains crystallites of oxometallates II of the novel structure type or consists exclusively of them (starting material 1), and then bringing the starting material 1 into intimate contact with suitable sources of the elemental constituents of the multimetal oxide material A $$Mo_{12} V_a X^1_b X^2_c X^3_d X^4_e X^5_f X^6_g O_x, \quad (A)$$

in the desired ratio and calcining the resulting dry mixture at from 250 to 500° C., it being possible to carry out the calcination under inert gas (eg. $N_2$), a mixture of inert gas and oxygen (eg. air), reducing gases, such as hydrocarbons (eg. methane), aldehydes (eg. acrolein) or ammonia or a mixture of $O_2$ and reducing gases (eg. all of the abovementioned ones), as described, for example, in DE-A 4 335 973. In a calcination under reducing conditions, it should be ensured that the metallic constituents are not reduced to the element. The duration of calcination is, as a rule, a few hours and usually decreases with increasing calcination temperature. As is generally known, all that is important with regard to the sources of the elemental constituents of the multimetal oxide material A is that they are either already oxides or are compounds which can be converted into oxides by heating, at least in the presence of oxygen. In addition to the oxides, particularly suitable starting compounds are halides, nitrates, formates, oxalates, citrates, acetates, carbonates and hydroxides. Suitable starting compounds of Mo, V, W and Nb are also oxo compounds thereof (molybdates, vanadates, tungstates and niobates) or the acids derived from these.

Crystallites of oxometallates II of the novel structure type can be prepared in a simple manner by producing a very intimate, preferably finely divided dry mixture whose composition corresponds to their stoichiometry from suitable sources of their elemental constituents, and calcining said dry mixture at from 700 to 900° C., preferably from 700 to 800° C., for several hours under inert gas or, preferably, in the air.

Surprisingly, either crystallites of oxometallates II of the novel structure alone or said crystallites as a mixture with crystallites of other oxometallate structure types are generally formed in the abovementioned high-temperature calcination.

The thorough mixing of the starting compounds can be carried out in dry or wet form. If it is effected in dry form, the starting compounds are advantageously used as finely divided powders and subjected to calcination after mixing and, if required, compaction. However, thorough mixing is preferably carried out in wet form. Usually, the starting compounds are mixed with one another in the form of an aqueous solution and/or suspension. Thereafter, the aqueous material is dried and then calcined. The drying process is preferably carried out directly after the production of the aqueous mixture and by spray-drying (the outlet temperatures are, as a rule, from 100 to 150 ° C.), which requires a particularly intimate dry mixture.

Particularly intimate dry mixtures are obtained in the drying process described when exclusively sources of the elemental constituents in salt form are used as starting materials. In the case of the elemental constituent copper, it is particularly advantageous in this context to start from aqueous solutions which contain it in the form of copper-ammonia complexes (eg. tetrammine).

The crystallites of oxometallates II of the novel structure type, which crystallites are obtainable as described above, or the crystallite mixtures containing them can then be used, for example by themselves as starting material 1, if necessary after milling and/or classification to desired sizes.

However, they may, of course, also be mixed beforehand with multimetal oxides $$X^7_{12} Cu_h H_i O_y$$

of other structure types, as listed, for example, in Table 1 and obtainable by the processes described in DE-A 44 05 514 and DE-A 44 40 891 (starting materials 1') in the desired ratio to give a novel starting material 1"). The latter can be used as such or, if required, first compressed, sintered, then comminuted again and then used.

The starting material 1 (or starting material 1") can be brought into intimate contact with the sources of the multimetal oxide material A (starting material 2) in both the dry and wet state. In the latter case, it is merely necessary to ensure that the pre-formed crystallites B* and, if necessary, other desired B crystallites do not go into solution. This is usually ensured in an aqueous medium at a pH which does not differ too greatly from 7. The said starting material is brought into intimate contact in the wet state, drying is usually subsequently effected to give a dry material (preferably by spray-drying). In dry mixing, such a dry material is automatically obtained. The starting material 1"" can of course also be brought into intimate contact with the sources of the multimetal oxide material A (starting material 2) in such a way that first a starting material 1 and then a starting material 1' are brought into contact, or vice versa.

For example, the following possible mixing methods are suitable:

a. mixing a dry, finely divided, pre-formed starting material 1 with dry, finely divided starting compounds of the elemental constituents of the desired multimetal oxide A in the desired ratio in a mixer, kneader or mill;

b. pre-forming a finely divided multimetal oxide A by thorough mixing of suitable starting compounds of its elemental constituents (dry or wet) and subsequently calcining the resulting intimate dry mixture at from 250 to 450° C. (the statements made on page 9 are applicable with regard to duration of calcination, calcination atmosphere and sources of elements); ensuring that the pre-formed multimetal oxide A is in finely divided form and mixing it with the finely divided starting material 1 in the desired ratio as in a.; in this mixing method, final calcination of the resulting mixture is not essential;

c. stirring the required amount of pre-formed starting material 1 into an aqueous solution and/or suspension of starting compounds of the elemental constituents of the desired multimetal oxide A and then carrying out spray-drying; instead of the starting compounds of the elemental constituents of the desired multimetal oxide A, it is of course also possible to use a multimetal oxide A itself which has already been preformed according to b.

All mixing methods intermediate between a., b. and/or c. can of course also be used. The resulting intimate dry mixture can then be calcined as described and thereafter molded to give the desired catalyst geometry, or vice versa. In principle, the calcined dry mixture (or, if desired, uncalcined dry mixture where mixing method b) is used) can however also be used as a powder catalyst.

Our own investigations have shown that the structure type of the crystallites B* contained in the starting material 1 is essentially retained as such on calcination of the dry mixture comprising the starting material 1 and the starting material 2. If the starting material 1 also contains other structure types of Table 1, these are likewise retained as such (particularly in the case of crystallites of oxometallates III of the wolframite structure type) or are partially or completely converted into other structure types of Table 1 on calcination of the dry mixture. However, essentially no fusion of the components of starting material 1 with those of starting material 2 takes place.

It is thus possible, after milling of the pre-formed starting mixture 1 or starting mixture 1' or starting mixture 1" (for example by wet or dry milling, for example in a ball mill or by jet milling), to separate off, from the resulting powder generally consisting of essentially spherical particles, the particle class having a maximum particle diameter in the maximum diameter range desired for the multimetal oxide material I (as a rule from >0 to 300 μm, preferably from 0.1 to 200 μm, particularly preferably from 0.5 to 50 μm, very particularly preferably from 1 to 30 μm) by classification to be carried out in a manner known per se (for example wet or dry screening) and thus to use it in a tailor-made manner for the preparation of the desired multimetal oxide material.

It is noteworthy that novel multimetal oxide materials I which are particularly advantageous as catalysts for the gas-phase catalytic oxidation of acrolein to acrylic acid are those whose promoter phase B contains both oxometallates II of the HT copper molybdate structure type (ie. crystallites B*) and crystallites of oxometallates III of the wolframite structure type (referred to here as crystallites B**). The weight ratio of crystallites B* to crystallites B** contained in the promoter phase B may be from 0.01 to 100, from 0.1 to 10, from 0.25 to 4 and from 0.5 to 2. This is true particularly when the promoter phase B of the novel multimetal oxide materials I consists exclusively of a mixture of such crystallites B* and crystallites B**, it being advantageous if the crystallites B* are ingrown with the crystallites B**.

Mixtures of crystallites B* of the general formula V and crystallites B** of the stoichiometry VI $$CuMo_{A'} W_{B'} V_{C'} O_{Y'}, \qquad (VI)$$

where
1/(A'+B'+C') is from 0.7 to 1.3,
A',B',C' are all >0, with the proviso that B'+C'≦1, and
Y' is a number which is determined by the valency and frequency of the elements other than oxygen in VI,
and/or of the stoichiometry VII

$$CuMo_{A'} W_{B'} O_{Y'},\qquad (VII)$$

where
1/(A'+B') is from 0.7 to 1.3,
B'/A' is from 0.01 to 1 and
Y' is a number which is determined by the valency and frequency of the elements other than oxygen in VII,
are preferred in this case.

Interestingly, such intergrown mixtures B*/B** are frequently formed in the calcination of intimate mixtures of suitable sources of their elemental constituents if the mixtures contain these elemental constituents in the stoichiometry III and if the calcination is carried out under inert gas or in air and at from 700 to 900° C.

When the novel multimetal oxide materials are used as catalysts for the gas-phase catalytic oxidation of acrolein to acrylic acid, shaping to give the desired catalyst geometry is preferably effected by application to premolded inert catalyst carriers, before or after the final calcination. The usual carriers, such as porous or nonporous aluminas, silica, thorium dioxide, zirconium dioxide, silicon carbide or silicates, such as magnesium silicate or aluminum silicate, may be used. The carriers may have a regular or an irregular shape, carriers having a regular shape and pronounced surface roughness, for example spheres or hollow cylinders, being preferred. Among these in turn, spheres are particularly advantageous. The use of essentially nonporous, spherical steatite carriers which have a rough surface and whose diameter is from 1 to 8 mm, preferably from 4 to 5 mm, is particularly advantageous. The layer thickness of the active material is advantageously chosen in the range from 50 to 500 μm, preferably from 150 to 250 μm. It should be pointed out here that, for coating the carriers in the preparation of such coated catalysts, the powder material to be applied is generally moistened and, after application, is dried again, for example by means of hot air.

For the preparation of the coated catalysts, the carriers are as a rule coated in a suitable rotatable container, as disclosed, for example, in DE-A 2909671 or EP-A 293859. As a rule, the relevant material is calcined before coating of the carrier.

The coating and calcination process according to EP-A 293 859 can be used in a suitable manner known per se if the resulting multimetal oxide active materials have a specific surface area of from 0.50 to 150 m²/g, a specific pore volume of from 0.10 to 0.90 cm³/g and a pore diameter distribution such that at least 10% of the total pore volume in each case are accounted for by the diameter ranges from 0.1 to <1 μm, from 1.0 to <10 μm and from 10 μm to 100 μm. The pore diameter distributions stated in EP-A 293 859 as being preferred may also be established.

The novel multimetal oxide materials can of course also be used as unsupported catalysts. In this context, the intimate dry mixture comprising starting materials 1 and 2 is preferably compacted directly to give the desired catalyst geometry (for example by pelletizing or extruding), it being possible, if required, to add conventional assistants, for example graphite or stearic acid as lubricants and/or molding assistants and reinforcing agents, such as microfibers of glass, asbestos, silicon carbide or potassium titanate, and is calcined. Here too, calcination may generally be carried out prior to the shaping procedure. A preferred geometry of unsupported catalysts is a hollow cylinder having an external diameter and a length of from 2 to 10 mm and a wall thickness of from 1 to 3 mm.

The novel multimetal oxide materials are particularly suitable as catalysts having high selectivity (at a given conversion) for the gas-phase catalytic oxidation of acrolein to acrylic acid. Acrolein produced by the catalytic gas-phase oxidation of propene is usually used in the process. As a rule, the acrolein-containing reaction gases of this propene oxidation are used without intermediate purification. The gas-phase catalytic oxidation of acrolein is usually carried out in tube-bundle reactors as a heterogeneous fixed-bed oxidation. Oxygen, advantageously diluted with inert gases (for example in the form of air), is used as the oxidizing agent in a manner known per se. Examples of suitable diluting gases are $N_2$, $CO_2$, hydrocarbons, recycled reaction exit gases and/or steam. As a rule, an acrolein:oxygen:steam:inert gas volume ratio of 1:(1 to 3):(0 to 20):(3 to 30), preferably 1:(1 to 3):(0.5 to 10):(7 to 18), is established in the acrolein oxidation. The reaction pressure is in general from 1 to 3 bar and the total space velocity is preferably from 1000 to 3500 l(S.T.P.) per l per h. Typical multitube fixed-bed reactors are described, for example, in DE-A 2 830 765, DE-A 2 201 528 or U.S. Pat. No. 3,147,084. The reaction temperature is usually chosen so that the acrolein conversion is above 90%, preferably above 98%, in a single pass. Usually, reaction temperatures of from 230 to 330° C. are required for this purpose.

It is noteworthy that the novel multimetal oxide materials also have a reduced forming time with respect to the selectivity of the acrylic acid formation in the gas-phase catalytic oxidation of acrolein to acrylic acid, ie. if a tube-bundle reactor loaded with the novel multimetal oxide materials is operated under the abovementioned conditions with an acrolein-containing gas stream for the purpose of the oxidative formation of acrylic acid, the selectivity of the acrylic acid formation actually reaches its plateau value within a reduced operating time. Furthermore, the preparation of the novel multimetal oxide materials exhibits high reproducibility with respect to this plateau value.

In addition to the gas-phase catalytic oxidation of acrolein to acrylic acid, the novel products are however also capable of catalyzing the gas-phase catalytic oxidation of other organic compounds, in particular other alkanes, alkanols, alkanals, alkenes and alkenols, preferably of 3 to 6 carbon atoms (eg. propylene, methacrolein, tert-butanol, the methyl ether of tert-butanol, isobutene, isobutane or isobutyraldehyde), to olefinically unsaturated aldehydes and/or carboxylic acids, and the corresponding nitriles (ammoxidation, especially of propene to acrylonitrile and of isobutene or tert-butanol to methacrylonitrile). The preparation of acrolein, methacrolein and methacrylic acid may be mentioned by way of example. However, they are also suitable for the oxidative dehydrogenation of olefinic compounds.

Finally, it should be stated that both the crystallites B* and the crystallites B** may also be used as key phases, in a manner completely analogous to that described above, in the multimetal oxide materials described and claimed in DE-A 44 05 058 and DE-A 44 05 060, and the resulting multimetal oxide materials may be used as gas-phase oxidation catalysts as described in the two DE-As.

Unless stated otherwise, the conversion, selectivity and residence time are defined as follows in this publication:

$$\text{Conversion C of acrolein (\%)} = \frac{\text{Number of moles of converted arcolein}}{\text{Number of moles of acrolein used}} \times 100;$$

$$\text{Selectivity S of the acrylic acid formation (\%)} = \frac{\text{Number of moles of converted arcolein converted into acrylic acid}}{\text{Total number of moles of acrolein converted}} \times 100;$$

$$\text{Residence time (sec)} = \frac{\text{Volume of reactor filled with catalyst (l)}}{\text{Synthesis gas through-put (l(S.T.P.)/h)}} \times 3600;$$

EXAMPLES a) Preparation of novel multimetal oxide materials M and multimetal oxide materials MV for comparison

MV1:

127 g of copper(II) acetate monohydrate (Cu content: 32.4% by weight) were dissolved in 2700 g of water to give a solution I. 860 g of ammonium heptamolybdate tetrahydrate (81.3% by weight of $MoO_3$), 143 g of ammonium metavanadate (72.2% by weight of $V_2O_5$) and 126 g of ammonium paratungstate heptahydrate (89.3% by weight of $WO_3$) were dissolved in succession in 5500 g of water at 95° C. to give a solution II. The solution I was then stirred all at once into the solution II, and the aqueous mixture was spray-dried at an outlet temperature of 110° C. The spray powder was then kneaded with 0.15 kg of water per kg of powder. The kneaded material was calcined in a through-circulation furnace fed with an oxygen/nitrogen mixture. The oxygen content was adjusted so that an $O_2$ content of 1.5% by volume was present at the outlet of the through-circulation furnace. During the calcination, the kneaded material was first heated at a rate of 10° C./min to 300° C. and then kept at this temperature for 6 hours. Thereafter, it was heated at a rate of 10° C./min to 400° C. and this temperature was maintained for a further hour. In order to adjust the ammonia content of the calcination atmosphere, the furnace loading F (g of catalyst precursor per l of internal volume of the through-circulation furnace), the inlet volume flow rate IF (l(S.T.P.)/h) of the oxygen/nitrogen mixture and the residence time RT (sec) of the oxygen/nitrogen feed (ratio of internal volume of the through-circulation furnace to volume flow rate of the oxygen/nitrogen mixture fed in) were chosen as listed below. The through-circulation furnace used had an internal volume of 3 l.

F: 250 g/l,
RT: 135 sec and
IF: 80 l(S.T.P.)/h.

The resulting catalytically active material is based on the following stoichiometry:

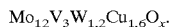
$Mo_{12}V_3W_{1.2}Cu_{1.6}O_x$.

After milling of the calcined, catalytically active material to particle diameters of from 0.1 to 50 μm, nonporous steatite spheres having a rough surface and a diameter of from 4 to 5 mm were coated with the resulting active material powder in an amount of 50 g of powder per 200 g of steatite spheres in a rotating drum, with simultaneous addition of 18 g of water. Drying was then effected with air at 110° C.

M1: Starting material 1:

371.76 g of ammonium heptamolybdate hydrate ($MoO_3$ content: 81.3% by weight, ideal composition: $(NH_4)_6 O_7O_{24}.4H_2O$) and 60.82 g of ammonium paratungstate hydrate ($WO_3$ content: 89.2% by weight, ideal composition: $(NH_4)_{10}W_{12}O_{41}.7H_2O$) were dissolved in 5 l of water at 90° C. while stirring (solution A). 3 l of water and 181.36 g of a 25% strength by weight aqueous ammonia solution were added to 455.68 g of copper acetate hydrate (Cu content: 32.5% by weight, ideal composition: $Cu(CH_3COO)_2.H_2O$) and stirring was carried out for 15 minutes at 25° C., a light blue aqueous suspension being obtained (suspension B). The suspension B was then stirred into the solution A which was at 90° C., the resulting aqueous suspension C was stirred for 3 hours at 80° C. After the resulting aqueous suspension C had been cooled to 25° C., this aqueous suspending medium had a pH of 5.0 (glass electrode). The suspension C was then spray-dried at an inlet temperature of 310° C. and an outlet temperature of 110° C. The resulting light green powder was calcined in air, heating being effected in a first step continuously in the course of 24 hours from 25° C. to 300° C. and in a subsequent second step continuously in the course of 3 hours from 300° C. to 780° C., and the temperature being kept at 780° C. for a further hour in a third step.

The calcination was carried out in a rotary furnace having a useful volume of 1 l, in each case 60 g of starting spray powder being used and an air stream of 50 l(S.T.P.)/h being established.

The resulting powder had a brown color, a specific surface area (determined according to DIN 66131 by gas adsorption ($N_2$) according to Brunauer-Emmet-Teller (BET)) of 0.3 $m^2/g$ and the composition $CuMo_{0.9}W_{0.1}O_{3.5-4}$. In the investigation by scanning electron microscopy (SEM), the powder had crystalline particles with a number average maximum particle diameter of about 8 μm. With the use of Cu Kα radiation (Siemens D-5000 diffractometer, 40 kV, 30 mA, with automatic divergence, antidiffusion and counter collimator and Peltier detector), the crystalline powder $CuMo_{0.9}W_{0.1}O_{3.5-4}$ showed the following X-ray diffraction pattern, reproduced in the form of interplanar spacings d[Å] independent of the wavelength of the X-rays used, and the associated relative intensities (%) of the various diffraction lines, based on the diffraction line of highest intensity (arranged according to decreasing intensity):

| d [Å] | Intensity [%] |
| --- | --- |
| 3.40 | 100 |
| 3.54 | 72 |
| 2.27 | 39 |
| 6.79 | 32 |
| 2.56 | 25 |
| 1.57 | 22 |
| 1.87 | 19 |
| 2.96 | 18 |
| 3.56 | 18 |
| 1.64 | 17 |
| 2.66 | 16 |
| 1.59 | 16 |
| 1.55 | 16 |
| 2.67 | 14 |
| 2.00 | 14 |
| 3.04 | 13 |
| 1.57 | 11 |
| 2.36 | 11 |
| 1.44 | 11 |
| 1.70 | 10 |
| 1.51 | 10 |
| 2.35 | 10 |

-continued

| d [Å] | Intensity [%] |
|---|---|
| 1.55 | 9.6 |
| 2.32 | 9.2 |
| 2.89 | 9.0 |
| 1.68 | 9.0 |
| 1.48 | 8.9 |
| 1.94 | 8.7 |
| 1.60 | 8.7 |
| 2.69 | 8.6 |
| 1.84 | 8.5 |
| 1.99 | 8.1 |
| 3.92 | 8.0 |
| 2.34 | 8.0 |
| 2.70 | 7.5 |
| 1.52 | 7.5 |
| 1.49 | 7.4 |
| 2.44 | 7.3 |
| 5.78 | 7.2 |
| 1.68 | 7.1 |
| 1.91 | 6.9 |
| 1.71 | 6.8 |
| 1.74 | 6.5 |
| 4.56 | 6.3 |
| 3.16 | 6.1 |
| 2.08 | 5.7 |
| 2.02 | 5.6 |
| 2.28 | 5.6 |
| 2.05 | 5.5 |
| 1.80 | 5.4 |
| 5.13 | 4.9 |
| 3.48 | 4.9 |
| 3.12 | 4.1 |
| 4.20 | 3.7 |
| 4.39 | 3.5 |
| 3.84 | 3.5 |
| 3.73 | 3.4 |
| 4.68 | 3.4 |
| 4.46 | 3.2 |
| 3.76 | 2.9 |

The inaccuracy of the interplanar spacings d is essentially ±0.3 Å for d values ≧2.9 Å and essentially ±0.2 Å for d values <2.9 Å (the low intensity lines may also include lines attributed to small amounts of impurities).

Starting material 2:

777.7 g of ammonium heptamolybdate tetrahydrate (81.3% by weight of $MoO_3$), 147.0 g of ammonium metavanadate (77.2% by weight of $V_2O_5$) and 112.1 g of ammonium paratungstate heptahydrate (89.3% by weight of $WO_3$) were dissolved in succession in 5500 g of water at 95° C. The aqueous solution (starting material 2) thus had the following stoichiometry:

$$Mo_{12}V_{3.41}W_{1.18}.$$

After milling in a centrifugal mill from Retsch, Germany, to a number average maximum particle diameter from 1 to 3 μm, the starting material 1 was stirred into the starting material 2 in an amount such that the molar ratio of the abovementioned stoichiometric units was 1.6 (starting material 1): 0.88 (starting material 2). Thereafter, 102.5 g of ammonium acetate were also stirred into the aqueous mixture and the resulting suspension was stirred for a further hour at 95° C. and then cooled to 80° C. The aqueous mixture was then spray-dried as in MV1 and further processed to give a coated catalyst whose active material thus likewise had the overall stoichiometry $Mo_{12}V_3W_{1.2}Cu_{1.6}O_x$ $$\triangleq [Mo_{12}V_{3.41}W_{1.18}O_x.]_{0.88}[CuMo_{0.9}W_{0.1}O_{3.5-4}]_{1.6}$$

Once again, the X-ray spectrum of the active material contained the HT Cu molybdate type.

MV2: Starting material 1:

263.83 g of ammonium heptamolybdate hydrate ($MoO_3$ content: 81.8% by weight, ideal composition: $(NH_4)_6Mo_7O_{24}.4H_2O$) and 260.26 g of ammonium paratungstate hydrate ($WO_3$ content: 89.0% by weight, ideal composition: $(NH_4)_{10}W_{12}O_{41}.7H_2O$) were dissolved in 4 l of water at 90° C. (solution A). 4 l of water and 435 g of 25% strength by weight aqueous ammonia solution were added to 496.37 g of copper acetate hydrate (Cu content: 32.0% by weight, ideal composition: $Cu(CH_3COO)_2.H_2O$) and stirring was carried out at 25° C. for 15 minutes, a blue solution being obtained (solution B). Thereafter, the solution B was stirred into the solution A which was at 90° C., and the resulting mixture was stirred for a further 3 hours at 70° C. After the resulting aqueous mixture C had been cooled to 25° C., its aqueous medium had a pH of 8.4 (glass electrode). The mixture C was then spray-dried at an inlet temperature of 330° C. and an outlet temperature of 110° C. The resulting green powder was calcined in air, heating being effected in a first step continuously in the course of 24 hours from 25 to 300° C. and in a subsequent second step continuously in the course of 12 hours from 300 to 400° C. and the temperature being kept at 400° C. for a further hour in a third step. Otherwise, the calcination was carried out as in the case of starting material 1 for M1.

The resulting powder had a brown color, a specific surface area according to DIN 66131 of 9.5 $m^2/g$ and the composition $CuMo_{0.6}W_{0.4}O_4$. In the SEM investigation, the powder exhibited spheres containing crystalline particles and having a number average particle maximum diameter of about 0.2 gm.

With the use of Cu Kα radiation (Siemens D-5000 diffractometer, 40 kV, 30 mA, with automatic divergence, antidiffusion and counter collimator and Peltier detector), the crystalline powder exhibited a powder X-ray pattern which corresponded to the wolframite structure type ($CuMoO_4$—III according to Russian Journal of Inorganic chemistry 36(7) (1991), 927, Table 1, or $CuWO_4$ according to index card 21-307 of the JCPDS-ICDD index (1994)).

A further phase over and above the wolframite structure was not present.

Starting material 2:

An aqueous solution was produced as in the case of M1 but the underlying stoichiometry was $$Mo_{12}V_{3.26}W_{0.61}.$$

After milling according to starting material 1 from M1, starting material 1 was stirred into the starting material 2 in an amount such that the molar ratio of the abovementioned stoichiometric units was 1.6 (starting material 1):0.92 (starting material 2).

The aqueous mixture was then treated as in M1, spray-dried and further processed to give a coated catalyst whose active material thus likewise had the overall stoichiometry $Mo_{12}V_3W_{1.2}Cu_{1.6}O_x$ $$\triangleq [Mo_{12}V_{3.26}W_{0.61}O_x.]_{0.92}[CuMo_{0.6}W_{0.4}O_4]_{1.6}$$

Once again, the X-ray spectrum of the active material contained the wolframite type.

M2: Starting material 1:

A spray-dried powder which contained the elements Cu, Mo and W in the molar ratio 1:0.6:0.4 was prepared in the same manner as the preparation of the starting material 1 for MV2. The resulting green powder was calcined in air, heating being effected in a first step continuously in the course of 24 hours from 25 to 300° C. and in a subsequent second step continuously in the course of 3 hours from 300 to 700 ° C. and the temperature being kept constant at 700° C. for a further hour in a third step. Otherwise, calcination was carried out as in the case of starting material 1 for M1.

The resulting powder had a brown color, a specific surface area according to DIN 66131 of 0.8 m²/g and the composition $CuMo_{0.6}W_{0.4}O_{3.5-4}$. In the SEM investigation, the powder had crystalline particles with a number average maximum particle diameter of about 8 μm. With the use of Cu Kα radiation (Siemens D-5000 diffractometer, 40 kV, 30 mA, with automatic divergence, antidiffusion and counter collimator and Peltier detector), the crystalline powder of the composition $CuMo_{0.6}W_{0.4}O_{3.5-4}$ gave a powder X-ray pattern which exhibited a superposition of the HT Cu molybdate fingerprint on the wolframite fingerprint, ie. it had a two-phase structure.

According to the line intensities, the two structure types were present with about the same frequency (about 50% by weight).

Starting material 2:

An aqueous solution was produced as in the case of M1 but the underlying stoichiometry was $Mo_{12}V_{3.26}W_{0.61}$.

After milling according to starting material 1 from M1, the starting material 1 was stirred into the starting material 2 in an amount such that the molar ratio of the abovementioned stoichiometric units was 1.6 (starting material 1):0.92 (starting material 2). Thereafter, the aqueous mixture was treated as in M1, spray-dried and further processed to give a coated catalyst whose active material thus likewise had the overall stoichiometry $Mo_{12}V_3W_{1.2}Cu_{1.6}O_x$ $\triangleq [Mo_{12}V_{3.26}W_{0.61}O_x.]_{0.92}[CuMo_{0.6}W_{0.4}O_{3.5-4}]_{1.6}$ Once again, the X-ray spectrum of the active material contained the superposition of HT Cu molybdate type and wolframite type.

MV3: Starting material 1:

223.05 g of ammonium heptamolybdate hydrate ($MoO_3$ content: 81.3% by weight, ideal composition: $(NH_4)_6Mo_7O_{24}.4H_2O$) and 327.52 g of ammonium paratungstate hydrate ($WO_3$ content: 89.2% by weight, ideal composition: $(NH_4)_{10}W_{12}O_{41}.7H_2O$) were dissolved in 5 l of water at 90° C. while stirring (solution A). 3 l of water and 197.88 g of a 25% strength by weight aqueous ammonia solution were added to 492.64 g of copper acetate hydrate (Cu content: 32.5% by weight, ideal composition: $Cu(CH_3COO)_2.H_2O$) and stirring was carried out for 15 minutes at 25° C., a light blue suspension being obtained (suspension B). The suspension B was then stirred into the solution A which was at 90° C., and the resulting suspension C was stirred for a further 3 hours at 80° C. After the resulting aqueous suspension C had been cooled to 25° C., the aqueous suspending medium had a pH of 5.3 (glass electrode). The suspension C was then spray-dried at an inlet temperature of 310° C. and an outlet temperature of 110° C. The resulting light green powder was calcined in air, heating being effected in a first step continuously in the course of 24 hours from 25 ° C. to 300° C. and in a subsequent second step continuously in the course of 1 hour from 300° C. to 400° C., and the temperature being kept at 400° C. for a further hour in a third step. Otherwise, the calcination was carried out as in the case of starting material 1 for M1.

The resulting powder had a brown color, a specific surface area according to DIN 66131 of 12.2 m²/g and the composition $CuMo_{0.5}W_{0.5}O_4$. In the SEM investigation, the powder exhibited spheres containing crystalline particles and having a number average maximum particle diameter of about 0.15 μm. With the use of Cu Kα radiation (Siemens D-5000 diffractometer, 40 kV, 30 mA, with automatic divergence, antidiffusion and counter collimator and Peltier detector), the crystalline powder of the composition $CuMo_{0.5}W_{0.5}O_4$ gave a powder X-ray pattern which corresponded to the wolframite structure type. A further phase over and above the wolframite structure was not present.

Starting material 2:

An aqueous solution was produced as in the case of M1 but the underlying stoichiometry was $Mo_{12}V_{3.21}W_{0.43}$.

The starting material 1 was stirred into starting material 2 in an amount such that the molar ratio of the abovementioned stoichiometric units was 1.6 (starting material 1):0.93 (starting material 2).

Thereafter, the aqueous mixture was treated as in M1, spray-dried and further processed to give a coated catalyst whose active material thus likewise had the overall stoichiometry $Mo_{12}V_3W_{1.2}Cu_{1.6}O_x$ $\triangleq [Mo_{12}V_{3.21}W_{0.43}O_x.]_{0.93}[CuMo_{0.5}W_{0.5}O_4]_{1.6}$ Once again, the X-ray spectrum of the active material contained the wolframite type.

M3: Starting material 1:

A spray-dried powder which contained the elements Cu, Mo and W in the molar ratio 1:0.5:0.5 was prepared in the same manner as the preparation of the starting material 1 for MV3. The resulting green powder was calcined in air, heating being effected in a first step continuously in the course of 24 hours from 25 to 300° C. and in a subsequent second step continuously in the course of 3 hours from 300 to 780° C. and the temperature being kept constant at 780° C. for a further hour in a third step. Otherwise, calcination was carried out as in the case of starting material 1 for M1.

The resulting powder had a brown color, a specific surface area according to DIN 66131 of 0.3 m²/g and the composition $CuMo_{0.5}W_{0.5}O_{3.5-4}$. In the SEM investigation, the powder had crystalline particles with a number average maximum particle diameter of about 8 μm. With the use of Cu Kα radiation (Siemens D-5000 diffractometer, 40 kV, 30 mA, with automatic divergence, antidiffusion and counter collimator and Peltier detector), the crystalline powder of the composition $CuMo_{0.5}W_{0.5}O_{3.5-4}$ gave a powder X-ray pattern which exhibited a superposition of the HT Cu molybdate fingerprint on the wolframite fingerprint, ie. it had a two-phase structure. According to the line intensities, the two structure types were present roughly in the frequency ratio 60 (wolframite structure):40 (HT Cu molybdate type).

Starting material 2:

An aqueous solution was produced as in the case of M1 but the underlying stoichiometry was $Mo_{12}V_{3.21}W_{0.43}$.

After milling according to starting material 1 from M1, the starting material 1 was stirred into the starting material 2 in an amount such that the molar ratio of the abovementioned stoichiometric units was 1.6 (starting material 1) to 0.93 (starting material 2).

The aqueous mixture was then treated as in M1, spray-dried and further processed to give a coated catalyst whose active material thus likewise had the overall stoichiometry $Mo_{12}V_3W_{1.2}Cu_{1.6}O_x$ $$\triangleq [Mo_{12}V_{3.21}W_{0.43}O_x]_{0.93}[CuMo_{0.5}W_{0.5}O_{3.5-4}]_{1.6}$$

Once again, the X-ray spectrum of the active material contained the superposition of wolframite type and HT Cu molybdate type.

b. Use of the coated catalysts from a. as catalysts for the gas-phase oxidation of acrolein to acrylic acid The catalysts were introduced into a tube reactor (V2A stainless steel, 25 mm internal diameter, 2000 g catalyst bed, heated by salt bath) and a gaseous mixture having the composition
5% by volume of acrolein,
7% by volume of oxygen,
10% by volume of steam and
78% by volume of nitrogen
was fed in at reaction temperatures of from 250 to 270° C. with the use of a residence time of 2.0 seconds. In all cases, the salt bath temperature was adjusted so that, after the end of formation, a single pass gave a uniform acrolein conversion C of 99%. The product gas mixture flowing out of the reactor was analyzed by gas chromatography. The results for the selectivity of the acrylic acid formation with the use of the various catalysts are shown in the table below.

| Catalyst | S (%) |
|----------|-------|
| MV1 | 95.3 |
| M1 | 95.6 |
| MV2 | 95.7 |
| M2 | 95.9 |
| MV3 | 96.1 |
| M3 | 96.5 |

We claim:

1. A process for the gas-phase catalytic oxidation of organic compounds, comprising oxidizing an organic compound is the presence of a catalyst, wherein said catalyst is a multimetal oxide material containing Cu, Mo and at least one of the elements W, V, Nb and Ta, having a multiphase structure and containing crystallites B* of an oxometallates of formula II $$Cu\ Mo_A W_B V_C Nb_D Ta_E\ \text{oxide} \qquad \text{(Formula II)},$$

where
1/(A+B+C+D+E) is from 0.7 to 1.3,
(B+C+D+E)/A is from 0.01 to 1,
wherein said oxometallate has a structure which is defined by the following X-ray diffraction pattern, reproduced in the form of interplanar spacings d[Å] independent of the wavelength of the X-rays used:
d[Å]
6.79±0.3
3.56±0.3
3.54±0.3
3.40±0.3
3.04±0.3
2.96±0.3
2.67±0.2
2.66±0.2
2.56±0.2
2.36±0.2
2.35±0.2
2.27±0.2
2.00±0.2
1.87±0.2
1.70±0.2
1.64±0.2
1.59±0.2
1.57±0.2
1.57±0.2
1.55±0.2
1.51±0.2
1.44±0.2.

2. The process of claim 1, wherein said multimetal oxide material is a multimetal oxide material of the formula I $$[A]_p[B]_q, \qquad \text{(Formula I)}$$

where

A is $Mo_{12}V_a X_b^1 X_c^2 X_d^3 X_e^4 X_f^5 X_g^6$ oxide (active phase),

B is $X_{12}^7 Cu_h H_i$ oxide (promoter phase), $X^1$ is at least one member selected from the group consisting of W, Nb, Ta, Cr and Ce, $X^2$ is at least one member selected from the group consisting of Cu, Ni, Co, Fe, Mn and Zn, $X^3$ is at least one member selected from the group consisting of Sb and Bi, $X^4$ is at least one member selected from the group consisting of Li, Na, K, Rb, Cs and H, $X^5$ is at least one member selected from the group consisting of Mg, Ca, Sr and Ba, $X^6$ is at least one member selected from the group consisting of Si, Al, Ti and Zr, $X^7$ is at least one member selected from the group consisting of Mo, W, V, Nb and Ta, a is from 1 to 8,
b is from 0.2 to 5,
c is from 0 to 23,
d is from 0 to 50,
e is from 0 to 2,
f is from 0 to 5,
g is from 0 to 50,
h is from 4 to 30,
i is from 0 to 20,
p and q are non-zero numbers whose ratio p/q is from 160:1 to 1:1, wherein said multimetal oxide material contains the component $[A]_p$ in the form of three-dimensional regions A which are delimited with respect to the local environment of said regions A owing to the chemical composition differences from the local environment and are of the chemical composition $$A\ Mo_{12}V_a X_b^1 X_c^2 X_d^3 X_e^4\ X_f^5 X_g^6\ \text{oxide} \qquad A$$

and the component $[B]_q$ in the form of three-dimensional regions B which are delimited from the local environment of said regions B owing to the chemical composition differences from the local environment and are of the chemical composition $$X_{12}^7Cu_hH_i \text{ oxide} \qquad B$$

with the proviso that the regions B contain said crystallites B* of oxometallates of formula II.

3. The process of claim 2, where $X^1$ is at least one member selected from the group consisting of W, Nb and Cr.

4. The process of claim 2, where $X^2$ is at least one member selected from the group consisting of Cu, Ni, Co and Fe.

5. The process of claim 2, where $X^4$ is at least one member selected from the group consisting of Na and K.

6. The process of claim 2, where $X^5$ is at least one member selected from the group consisting of Ca, Sr and Ba.

7. The process of claim 2, where $X^6$ is at least one member selected from the group consisting of Si, Al and Ti.

8. The process of claim 2, where $X^7$ is at least one member selected from the group consisting of Mo and W.

9. The process of claim 2, where said regions A have a composition according to following formula IV $$Mo_{12}V_aX_b^1X_c^2X_f^5X_g^6 \text{ oxide} \qquad \text{(Formula IV)},$$

where $X^1$ is at least one member selected from the group consisting of W and Nb, $X^2$ is at least one member selected from the group consisting of Cu and Ni, $X^5$ is at least one member selected from the group consisting of Ca and Sr, $X^6$ is at least one member selected from the group consisting of Si and Al, a' is from 2 to 6, b' is from 1 to 2, c' is from 1 to 3, f' is from 0 to 0.75, and g' is from 0 to 10.

10. The process of claim 2, where said regions B additionally contain crystallites B** of oxometallates of formula III $$CuMo_{A'}W_{B'}V_{C'}Nb_{D'}Ta_{E'} \text{ oxide}.(H_2O)_{F'}, \qquad \text{(Formula III)},$$

where $1/(A'+B'+C'+D'+E')$ is from 0.7 to 1.3,

F' is from 0 to 1, and

B'+C'+D'+E' is from 0 to 1 said crystallites B** having the structure which is defined by the compound Cu—MoO$_4$—III.

11. The process of claim 10, where said crystallites B** have formula VI $$CuMo_{A'}W_{B'}V_{C'} \text{oxide} \qquad \text{(Formula VI)},$$

where $1/(A'+B'+C')$ is from 0.7 to 1.3, and

A', B' and C' are all>0, with the proviso that B'+C' is $\leq 1$, or Formula VII $$CuMo_{A'}W_{B'} \text{ oxide} \qquad \text{(Formula VII)},$$

where $1/(A'+B')$ is from 0.7 to 1.3, and

B'/A' is from 0.01 to 1.

12. The process of claim 1, where said catalyst further contains oxometallates of formula III $$CuMo_{A'}W_{B'}V_{C'}Nb_{D'}Ta_{E'} \text{ oxide}.(H_2O)_{F'} \qquad \text{(Formula III)},$$

where $1/(A'+B'+C'+D'+E')$ is from 0.7 to 1.3,

F' is from 0 to 1, and

B'+C'+D'+E' is from 0 to 1 wherein said oxometallates of formula III have the wolframite structure.

13. The process of claim 10, where said regions B contain exclusively crystallites B* of oxometallates of formula II and crystallites B** of oxometallates of formula III.

14. The process of claim 2, where said multimetal oxide material is prepared by a process wherein an oxometallate $$X_{12}^7Cu_hH_i \text{ oxide}, \qquad B$$

which contains crystallites B* is pre-formed in finely divided form as starting material and the starting material is then brought into intimate contact with a composition comprising the elemental constituents of a multimetal oxide A $$Mo_{12}V_aX_b^1X_c^2X_d^3X_e^4X_f^5X_g^6 \text{ oxide} \qquad A$$

and a resulting dry mixture is calcined at from 250 to 500° C.

15. The process of claim 14, wherein crystallites B* are an oxometallate of formula II $$Cu\ Mo_AW_BV_CNb_DTa_E \text{ oxide} \qquad \text{(Formula II)},$$

where $1/(A+B+C+D+E)$ is from 0.7 to 1.3, $(B+C+D+E)/A$ is from 0.01 to 1, wherein said oxometallate has a structure which is defined by the following X-ray diffraction pattern, reproduced in the form of interplanar spacings d[Å] independent of the wavelength of the X-rays used:

d[Å]
6.79±0.3
3.56±0.3
3.54±0.3
3.40±0.3
3.04±0.3
2.96±0.3
2.67±0.2
2.66±0.2
2.56±0.2
2.36±0.2
2.35±0.2
2.27±0.2
2.00±0.2
1.87±0.2
1.70±0.2
1.64±0.2
1.59±0.2
1.57±0.2
1.57±0.2
1.55±0.2
1.51±0.2
1.44±0.2.

16. The process of claim 15, wherein said oxometallate $$X_{12}^7Cu_hH_i \text{ oxide}, \qquad B$$

further contain crystallites B** of an oxometallate of formula III $CuMo_{A'}W_{B'}V_{C'}Nb_{D'}Ta_{E'}$ oxide.$(H_2O)_{F'}$ (Formula III), where 1/(A'+B'+C'+D'+E') is from 0.7 to 1.3, F' is from 0 to 1, and B'+C'+D'+E' is from 0 to 1 wherein said oxometallates of formula III have the wolframite structure or distorted wolframite structure.

17. The process of claim 1, where said oxometallate is prepared by a process wherein sources of the elements constituting the oxometallates are thoroughly mixed with one another and the resulting intimate mixture is calcined in air or under inert gas at from 700 to 900° C.

18. The process of claim 12, where said oxometallate is prepared by a process wherein sources of the elements constituting the oxometallates are thoroughly mixed with one another and the resulting intimate mixture is calcined in air or under inert gas at from 700 to 900° C.

19. The process of claim 1, where said oxometallate is prepared by a process, comprising:

forming a mixture comprising the oxometallate of formula II.

20. The process of claim 12, where said oxometallate is prepared by a process, comprising:

forming a mixture comprising the oxometallate of formula II.

21. The process of claim 2, where $X^3$ is Sb.
22. The process of claim 2, where a is from 2 to 6.
23. The process of claim 2, where b is from 0.5 to 2.5.
24. The process of claim 2, where c is from 0 to 4.
25. The process of claim 2, where d is from 0 to 3.
26. The process of claim 2, where e is from 0 to 0.3.
27. The process of claim 2, where f is from 0 to 2.
28. The process of claim 2, where g is from 0 to 20.
29. The process of claim 2, where h is from 6 to 24.
30. The process of claim 2, where h is from 9 to 17.
31. The process of claim 2, where i is from 0 to 10.
32. The process of claim 2, where p/q is from 20:1 to 1:1.
33. The process of claim 2, where p/q is from 15:1 to 1:1.
34. The process of claim 2, wherein said multimetal oxide material contains the component $[B]_q$ in the form of three-dimensional regions of chemical composition B whose maximum diameters $d_B$ are from >0 to 300 μm.
35. The process of claim 2, wherein said multimetal oxide material contains the component $[B]_q$ in the form of three-dimensional regions of chemical composition B whose maximum diameters $d_B$ are from 0.1 to 200 μm.
36. The process of claim 2, wherein said multimetal oxide material contains the component $[B]_q$ in the form of three-dimensional regions of chemical composition B whose maximum diameters $d_B$ are from 0.5 to 50 μm.
37. The process of claim 2, wherein said multimetal oxide material contains the component $[B]_q$ in the form of three-dimensional regions of chemical composition B whose maximum diameters $d_B$ are from 1 to 30 μm.
38. The process of claim 2, where 1/(A+B+C+D+E) is from 0.85 to 1.15.
39. The process of claim 2, where 1/(A+B+C+D+E) is from 0.95 to 1.05.
40. The process of claim 2, where 1/(A+B+C+D+E) is 1.
41. The process of claim 2, where (B+C+D+E)/A is from 0.05 to 0.3.
42. The process of claim 2, where (B+C+D+E)/A is from 0.075 to 0.15.
43. The process of claim 2, where (B+C+D+E)/A is 0.11.
44. The process of claim 2, where C+D+E is 0.
45. The process of claim 2, wherein the oxometallate II has the composition $Cu_1Mo_{0.9}W_{0.1}O_{3.5-4}$.
46. The process of claim 2, whose regions B additionally contain crystallites which have the structure type of one or more of the copper molybdates listed below:

| | |
|---|---|
| $Cu_3(MoO_4)_2(OH)_2$ | (lindgrenite, index card 36-405 of the JCPDS-ICDD index (1991)), |
| $Cu_4MoO_6O_{20}$ | (A. Moini et al., Inorg. Chem. 25 (21) (1986) pages 3782 to 3785), |
| $Cu_4Mo_5O_{17}$ | (index card 39-181 of the JCPDS-ICDD index (1991)), |
| $Cu_6Mo_5O_{18}$ | (index card 40-865 of the JCPDS-ICDD index (1991)), |
| $Cu_6Mo_4O_{15}$ | (index card 35-17 of the JCPDS-ICDD index (1991)), |
| $CuMoO_4$ | (index card 22-242 of the JCPDS-ICDD index (1991)), |
| $CuMoO_4$ | (Russian Journal of Inorganic Chemistry 36 (7), (1991), 927-928, Table 1, $CuMoO_4$-III with distorted wolframite structure ($CuWO_4$, index card 21-307 of the JCPDS-ICDD index (1994)), |
| $Cu_{4-x}Mo_3O_{12}$ | where x = 0 to 0.25 (index cards 24-56 and 26-547 of the JCPDS-ICDD index (1991)), |
| $Cu_3Mo_2O_9$ | (index cards 24-55 and 34-637 of the JCPDS-ICDD index (1991)), |
| $Cu_2MoO_5$ | (index card 22-607 of the JCPDS-ICDD index (1991)). |

47. The process of claim 2, where the amount of crystallites B* is from >0 to 100 or from 1 to 95 or from 5 to 90 or from 10 to 85 or from 15 to 75 or from 25 to 65 or from 35 to 55 or from 40 to 50% by weight, based on the total weight of the component $[B]_q$.

48. The process of claim 1, where 1/(A+B+C+D+E) is from 0.85 to 1.15.

49. The process of claim 1, where 1/(A+B+C+D+E) is from 0.95 to 1.05.

50. The process of claim 1, where 1/(A+B+C+D+E) is 1.

51. The process of claim 1, where (B+C+D+E)/A is from 0.05 to 2.

52. The process of claim 1, where (B+C+D+E)/A is from 0.075 to 0.15.

53. The process of claim 1, (B+C+D+E)/A is 0.11.

54. The process of claim 1, where C+D+E is 0.

55. The process of claim 1, wherein said oxometallates have the composition $Cu_1Mo_{0.9}W_{0.1}O_{3.5-4}$.

56. The process of claim 2, wherein said organic compound is acrolein.

57. The process of claim 1 wherein said organic compound is acrolein.

* * * * *